US00PP12998P2

(12) United States Plant Patent
Pieters

(10) Patent No.: US PP12,998 P2
(45) Date of Patent: Sep. 24, 2002

(54) CHRYSANTHEMUM PLANT NAMED 'PAPIRO'

(76) Inventor: Dirk Pieters, Schierveldestraat 3A, Oosnieuwkerke, 8840 Staden (BE)

( * ) Notice: Subject to any disclaimer, the term of this patent is extended or adjusted under 35 U.S.C. 154(b) by 0 days.

(21) Appl. No.: 09/550,157

(22) Filed: Apr. 17, 2000

(51) Int. Cl.[7] ..... A01H 5/00
(52) U.S. Cl. ..... Plt./294
(58) Field of Search ..... Plt./294

(56) References Cited

U.S. PATENT DOCUMENTS

PP5,367 P * 12/1984 Culbert ..... Plt./294
PP6,058 P * 12/1987 Duffett ..... Plt./294
PP6,222 P * 7/1988 Shoesmith ..... Plt./294
PP6,590 P * 2/1989 Sueptitz ..... Plt./294
PP6,999 P * 8/1989 VandenBerg ..... Plt./294
PP7,885 P * 6/1992 Fuess ..... Plt./294
PP8,609 P * 2/1994 VandenBerg ..... Plt./294
PP10,218 P * 1/1998 Pieters ..... Plt./294
PP11,294 P * 3/2000 Boeder ..... Plt./294

* cited by examiner

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new plant variety of chrysanthemum producing flowers with white ray florets and orange disc florets.

1 Drawing Sheet

BACKGROUND OF THE INVENTION

The present invention is directed to a new and distinct variety of chrysanthemum morifolium. The varietal denomination of the new chrysanthemum is 'PAPIRO'.

The new variety is a cross of 'Scorpio' (believed to be unpatented) as seed parent and 'Tripoli' (U.S. Plant Pat. No. 10,207) as pollen parent. The new variety has been asexually reproduced by vegetative cuttings in Ventura County, Calif. and the distinguishing characteristics are retained through successive generations of asexual reproduction.

SUMMARY OF THE INVENTION

'PAPIRO' is a chrysanthemum plant that produces flowers with white ray florets and orange disc florets.

COMPARISON WITH PARENTS

'PAPIRO' differs from its parent 'Scorpio' in having larger flowers and from its parent 'Tripoli' in having white ray florets whereas the parent has purple ray florets.

COMPARISON WITH OTHER VARIETIES

The following is a comparison to the commercial varieties 'GEDI WT8' (U.S. Plant Pat. No. 11,648), 'Pidoul' and 'Empire Aspen' (U.S. Plant Pat. No. 7,885):

| | 'GEDI WT8' | 'PAPIRO' | 'Pidoul' | 'Empire Aspen' |
|---|---|---|---|---|
| Inflorescence Diameter | 4.5 cm | 6 cm | 2.5 to 3 cm | 5 cm |
| Ray Floret coloration when mature | Near 158D | Near 155D | Near 155D | Near 155D |
| Quantity of Ray florets | About 30 | Between 50 to 60 | About 30 | Between 45 to 50 |

-continued

| | 'GEDI WT8' | 'PAPIRO' | 'Pidoul' | 'Empire Aspen' |
|---|---|---|---|---|
| Quantity of Inflorescence per stem | About 12 | About 15 | Between 12 to 15 | About 8 |
| Height | About 18 cm | About 23 cm | Between 25 to 30 cm | About 20 cm |
| Natural Season Bloom | Early October | End of September | Mid-September | First week of September |
| General Commercial Comparison | 'PAPIRO' has pure white ray florets and longer lasting inflorescence | | 'PAPIRO' has larger ray florets and longer lasting inflorescence | 'PAPIRO' has a larger number of inflorescence and a much more flexible plant form |

BRIEF DESCRIPTION OF ILLUSTRATIONS

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. The age of the described plant is approximately 120 days old from a rooted cutting. 'PAPIRO' has not been observed under all possible environmental conditions. The phenotype may vary with variations in the environment such as temperature, light intensity, day length and cultural conditions. The color designations herein are from The Royal Horticutural Society Colour Chart except where general terms are used.

To produce a commercial product the plants may be pinched once about ten days after planting. No growth retardant has been applied in the specimens described. Useful growing conditions include average night temperatures of about 17° C. to 20° C. and average day temperatures of about 20° C. to 30° C. No susceptibility or resistance to disease has been observed. Resistance or susceptibility to insects has not been observed. Seed production has not been observed. Winter hardiness and drought/heat tolerance have not been observed.

ROOTING CHARACTERISTICS

Time to initiate roots: About 7 to 14 days at about 21° C.
Root Description: Fine, fibrous.

PLANT

Plant type: Herbaceous perennial.
Growth habit: Mounding.
Size: Length about 23 cm, width about 25 cm.
Growth rate: Moderate.
Branching characteristics: Very free branching, lateral branches are about 20 cm in length, 0.5 cm in diameter and near 138C in color.

FOLIAGE

Arrangement: Alternate.
Compound or Simple: Simple.
Quantity of leaves: Many.
Leaf size:
*Length*.—About 6 cm.
*Width*.—About 4 cm.
Leaf shape: Ovate.
Leaf tip: Acuminate.
Leaf base: Attenuate.
Leaf attachment: Stalked.
Petiole: Length about 2 cm, diameter about 0.3 cm, color near 137C.
Margin type: Serrate.
Texture: Lightly pubescent.
Color:
*Young foliage upper side*.—Near 138A.
*Young foliage under side*.—Near 138B.
*Mature foliage upper side*.—Near 137A.
*Mature foliage under side*.—Near 138B.
Venation: Net.
*Color*.—Venation upper side: Near 137C. Venation under side: Near 137D.

BLOOM

Inflorescence:
*Flowering habit*.—Induced by darkness period greater than 13.5 hours. Approximately 50 days of day length required to induce and develop blooms.
*Inflorescence form*.—Daisy.
*Natural flowering season*.—Around the last week in September and early October in Ventura County, Calif.
*Quantity of inflorescences per stem*.—About 15.
*Length*.—About 1 cm.
*Width*.—About 0.1 cm.
*Color*.—First opening: Near 23A. Mature: Near 23B. Fading: Near 24B.

Peduncle:
*Length*.—Terminal, shortest: About 4 cm. Lateral, longest: About 8 cm.
*Diameter*.—About 0.3 cm.
*Color*.—Near 138A.
*Strength*.—Moderate.
*Habit*.—Erect.
Inflorescence bud:
*Length*.—About 1 cm.
*Diameter*.—About 1 cm.
*Form or shape*.—Globular.
*Color*.—Near 18D.
Involucral bracts: Length about 0.7 cm, width about 0.4 cm.
*Appearance*.—Matte.
*Texture*.—Lightly pubescent.
*Number*.—About 20 to 30.
*Shape*.—Ovate.
*Margin*.—Entire.
*Tip*.—Acute.
*Color*.—Upper side: Near 138A. Under side: Near 138A.
*Inflorescence diameter*.—About 6 cm.
*Inflorescence depth*.—About 2 cm.
*Disc diameter*.—About 2 cm.
*Inflorescence longevity on plant*.—About 18 to 22 days.
*Persistence*.—Persistent.
Ray florets:
*Appearance*.—Matte.
*Texture*.—Smooth.
*Number*.—About 50 to 60.
*Shape*.—Oblanceolate.
*Margin*.—Entire.
*Pistil*.—Length about 0.8 cm.
*Tip*.—Obtuse.
*Length*.—About 2 cm.
*Width*.—About 1 cm.
*Color*.—Upper side: First opening: Near 13D. Mature: Near 155D. Fading: Near 155D. Under side: First opening: Near 18D. Mature: Near 155D. Fading: Near 155D.
Disc florets:
*Appearance*.—Shiny.
*Texture*.—Smooth.
*Number*.—Over 200.
*Shape*.—Cylindric.
*Pistil*.—Length about 0.5 cm.
*Tip*.—Obtuse.

REPRODUCTIVE ORGANS

Ray florets:
*Pistillate*.—Pistil number: 1 per flower. Stigma shape: 2 branched. Stigma color: Near 7D. Style length: About 1 cm. Style color: Near 6D.
Disc florets:
*Pistillate*.—Pistil number: 1 per flower. Stigma shape: Cylindric. Style length: About 0.8 cm.
*Staminate*.—Stamen number: About 5. Anther shape: Tubular. Anther color: Near 16A. Pollen color: Near 20A.

What is claimed is:

1. A new and distinct chrysanthemum plant of the variety substantially as herein shown and described.

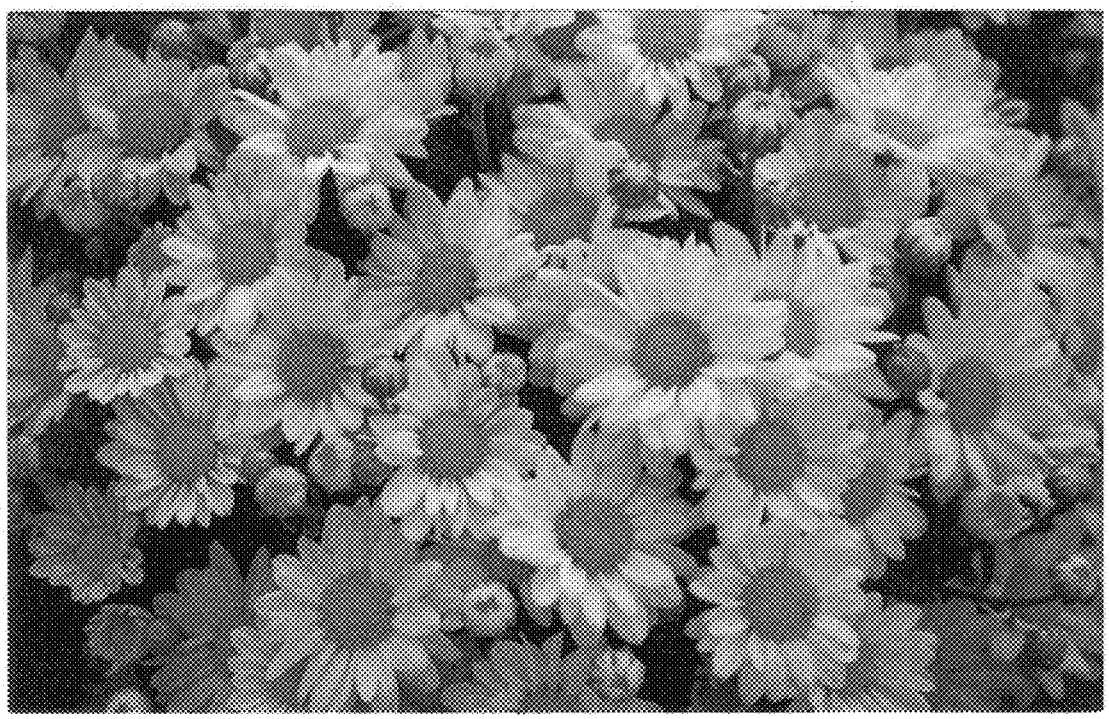

* * * * *